United States Patent
Li et al.

(10) Patent No.: US 10,432,073 B2
(45) Date of Patent: Oct. 1, 2019

(54) MEDICAL PUMP

(71) Applicant: JOHNSON ELECTRIC INTERNATIONAL AG, Murten (CH)

(72) Inventors: Yue Li, Hong Kong (CN); Chui You Zhou, Shenzhen (CN); Yan Ling Liu, Shenzhen (CN); Gui Hua Li, Shenzhen (CN); Xiao Ning Zhu, Shenzhen (CN); Yong Wang, Shenzhen (CN)

(73) Assignee: JOHNSON ELECTRIC INTERNATIONAL AG, Murten (CH)

( * ) Notice: Subject to any disclaimer, the term of this patent is extended or adjusted under 35 U.S.C. 154(b) by 245 days.

(21) Appl. No.: 15/422,739

(22) Filed: Feb. 2, 2017

(65) Prior Publication Data
US 2017/0222526 A1 Aug. 3, 2017

(30) Foreign Application Priority Data
Feb. 2, 2016 (CN) .......................... 2016 1 0074173

(51) Int. Cl.
| | | |
|---|---|---|
| *H02K 21/00* | (2006.01) | |
| *H02K 21/14* | (2006.01) | |
| *A61M 11/02* | (2006.01) | |
| *H02K 1/14* | (2006.01) | |
| *H02K 1/27* | (2006.01) | |
| *H02K 3/28* | (2006.01) | |
| *H02K 21/18* | (2006.01) | |

(52) U.S. Cl.
CPC ............. *H02K 21/14* (2013.01); *A61M 11/02* (2013.01); *H02K 1/141* (2013.01); *H02K 1/2706* (2013.01); *H02K 3/28* (2013.01); *H02K 21/18* (2013.01); *A61M 2205/0272* (2013.01)

(58) Field of Classification Search
CPC ....... H02K 1/141; H02K 1/274; H02K 1/2706
USPC .............................. 310/162, 216.037, 49.49; 30/156.01–156.84, 68 A, 68 B
See application file for complete search history.

(56) References Cited

U.S. PATENT DOCUMENTS

| | | | |
|---|---|---|---|
| 3,826,941 A | 7/1974 | Folmar | |
| 4,311,934 A * | 1/1982 | Flaig ...................... | G04C 13/11 |
| | | | 310/216.035 |

(Continued)

FOREIGN PATENT DOCUMENTS

| | | |
|---|---|---|
| CN | 202954989 U | 5/2013 |
| DE | 19533076 A1 | 3/1997 |
| JP | 2002257032 A | 9/2002 |

*Primary Examiner* — Hanh N Nguyen
(74) *Attorney, Agent, or Firm* — Muncy, Geissler, Olds & Lowe, P.C.

(57) ABSTRACT

A medical pump includes a single phase synchronous motor, a rod piston, a cylinder for receiving the rod piston for reciprocating motion therein. The single phase synchronous motor includes a stator and a rotor rotatable relative to the stator. The rotor includes a plurality of permanent magnets. The stator comprises a stator core and a winding wound around the stator core. The stator core comprises two opposed pole portions that define there between a rotor receiving space for receiving the permanent magnets. The medical pump has a compact structure. In addition, the motor of the medical pump has a constant rotation speed and has a smaller size and less weight under the same output power conditions as traditional motors used in medical pumps. The medical pump is particularly suitable for use in atomizers.

17 Claims, 7 Drawing Sheets

(56) References Cited

U.S. PATENT DOCUMENTS

| | | | |
|---|---|---|---|
| 4,691,132 A | 9/1987 | Bertram et al. | |
| 4,714,851 A * | 12/1987 | Bertram | H02K 21/185 |
| | | | 310/156.38 |
| 2010/0052455 A1* | 3/2010 | Feng | H02K 1/276 |
| | | | 310/156.08 |
| 2010/0176680 A1* | 7/2010 | Murakami | H02K 1/278 |
| | | | 310/156.38 |
| 2011/0043067 A1* | 2/2011 | Li | H02K 1/141 |
| | | | 310/158 |
| 2013/0088114 A1 | 4/2013 | Yamashita et al. | |
| 2013/0177394 A1* | 7/2013 | Yamada | F03C 1/0623 |
| | | | 415/10 |
| 2013/0249330 A1 | 9/2013 | King et al. | |

\* cited by examiner

MEDICAL PUMP

CROSS REFERENCE TO RELATED APPLICATIONS

This non-provisional patent application claims priority under 35 U.S.C. § 119(a) from Patent Application No. 201610074173.7 filed in The People's Republic of China on 2 Feb. 2016.

FIELD OF THE INVENTION

This invention relates to a medical device, and in particular to a medical pump.

BACKGROUND OF THE INVENTION

Motors are an important component of current medical pumps. The motor performance is of critical importance for the pump to spray mist uniformly. The motor size and cost are also important factors that affect the size and cost of the pump itself.

SUMMARY OF THE INVENTION

Thus, there is a desire for a medical pump to address the above problem.

A medical pump is provided which includes a single phase synchronous motor. The single phase synchronous motor comprises a stator and a rotor rotatable relative to the stator. The rotor includes a plurality of permanent magnets. The stator comprises a stator core and a winding wound around the stator core. The stator core comprises two opposed pole portions that define therebetween a rotor receiving space for receiving the permanent magnets.

Preferably, the stator core comprises two opposed pole portions that define therebetween a receiving space, and the permanent magnets are received in the receiving space and forms two permanent magnetic poles facing the pole portions of the stator.

Preferably, an outer surface of each of the permanent magnet is an arc surface and the permanent magnets of the rotor and the pole portions of the stator define therebetween an air gap with an uneven thickness.

Preferably, the distance from the outer surface of each of the permanent magnetic poles to an axis of the rotor decreases progressively from a circumferential center toward two circumferential ends of the outer surface of the permanent magnetic pole, and the thickness of the air gap increases progressively from the circumferential center toward the two circumferential ends of the permanent magnetic pole.

Preferably, the medical pump further comprises a U-shaped bracket, the bracket surrounds an end of the stator core that defines the two pole portions.

Preferably, outer surfaces of the stator core form first grooves or ribs, inner surfaces of the bracket form first ribs or grooves, and the first grooves and the first ribs are engaged to attach the stator core to the bracket.

Preferably, the two opposed pole portions are separated apart, the bracket forms a rib that extends into a gap formed between the two opposed pole portions.

Preferably, the stator further comprises a frame and a cover respectively mounted to a bottom and a top of the bracket, the stator core is axially positioned between the frame and the cover, and the rotor is rotatably mounted to the frame and the cover.

Preferably, the stator core comprises a [-shaped first core part and a]-shaped second core part that are spliced in a face-to-face fashion, a first end of the first core part and a first end of the second core part respectively form the pole portions, a second end of the first core part and a second end of the second core part are connected with each other.

Preferably, the medial pump further comprises an AC-DC conversion circuit and a bidirectional AC switch. An external AC power and the stator winding of the motor are connected in series between a first node and a second node, and the AC-DC conversion circuit and the bidirectional AC switch are connected in parallel between the first node and the second node.

Preferably, the rotor rotates at a constant speed of 3000 RPM or 3600 RPM during a steady state.

Preferably, the synchronous motor has an input power of 45 W to 50 W and an electrical current of 0.4 A to 0.6 A.

Preferably, the stator core has a length of 50 mm to 65 mm and a width L2 of 20 mm to 30 mm.

Preferably, the pump further comprises a rod piston driven by the single phase synchronous motor and a cylinder for receiving the rod piston for reciprocating motion therein.

Preferably, the single phase motor further comprises a driving circuit, the stator winding adapted to be connected in series with an AC power source between a first node and a second node, the driving circuit comprising: a controllable bidirectional AC switch connected between the first node and the second node; an AC-DC conversion circuit connected in parallel with the controllable bidirectional AC switch between the first node and the second node; a position sensor configured to detect a magnetic pole position of the permanent magnet rotor; and a switch control circuit configured to control the controllable bidirectional AC switch to be switched between a switch-on state and a switch-off state in a predetermined way, based on the magnetic pole position of the permanent magnet rotor and the polarity of the AC power source such that the stator winding drives the rotor to rotate only in the predetermined direction. There is no current flowing through the AC-DC conversion circuit when the first node and the second node are short circuited by the controllable bidirectional AC switch.

In summary, the present invention provides a medical pump. The medical pump utilizes a single phase synchronous motor that provides a constant rotation speed immune to voltage variations and has a small size.

Technical solutions of the invention will become apparent by consideration of the detailed description, claims and accompanying drawings.

BRIEF DESCRIPTION OF THE DRAWINGS

These and other features of the present invention will become readily apparent upon further review of the following specification and drawings. The figures are for the purposes of illustration only and should not be regarded as limiting. The figures are listed below.

DETAILED DESCRIPTION OF THE PREFERRED EMBODIMENTS

Figure 1:
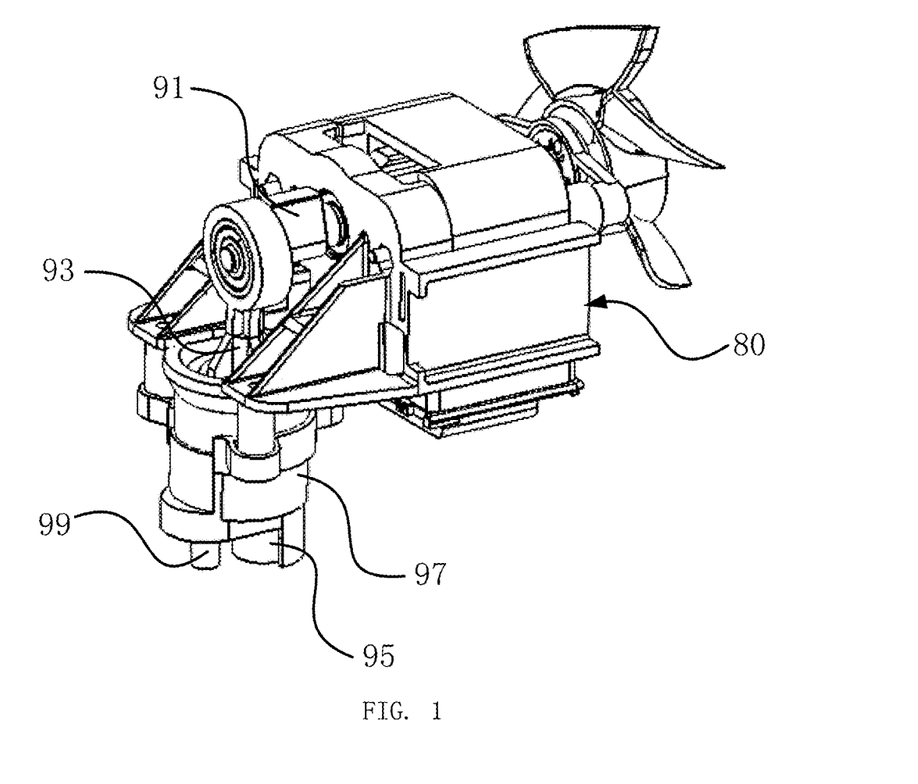
FIG. 1 illustrates a medical pump according to an embodiment of the present invention.
Figure 2:
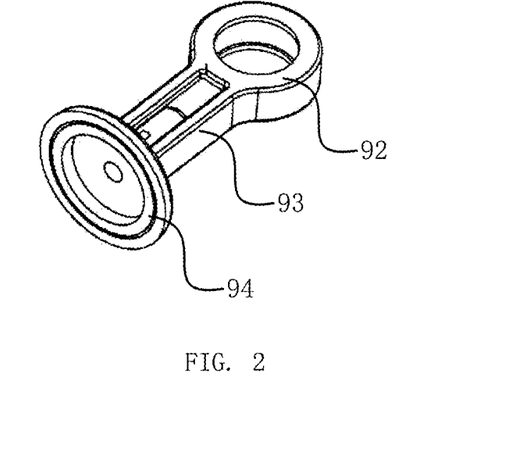
FIG. 2 illustrates a rod piston of the medical pump of FIG. 1.

Referring to FIG. 1 and FIG. 2, the present invention provides a medical pump. The medical pump includes a motor 80, an eccentric crank 91 mounted to an output shaft of the motor 80, a rod piston 93, and a cylinder 97. One end of the rod piston 93 includes a ring body 92 connected with the eccentric crank 91 and hence driven by the eccentric crank 91, and the other end of the rod piston 93 includes a piston 94. The other end of the rod piston 93 is accommodated in the cylinder 97 so that the piston 94 of the rod piston 93 can move reciprocatingly in the cylinder 97. The cylinder 97 has an inlet 95 and an outlet 99. During operation, the motor 80 drives the rod piston 93 to move reciprocatingly in the cylinder 97, which in turn compresses fluid such as air that sprays out via the outlet 99.

Figure 3:
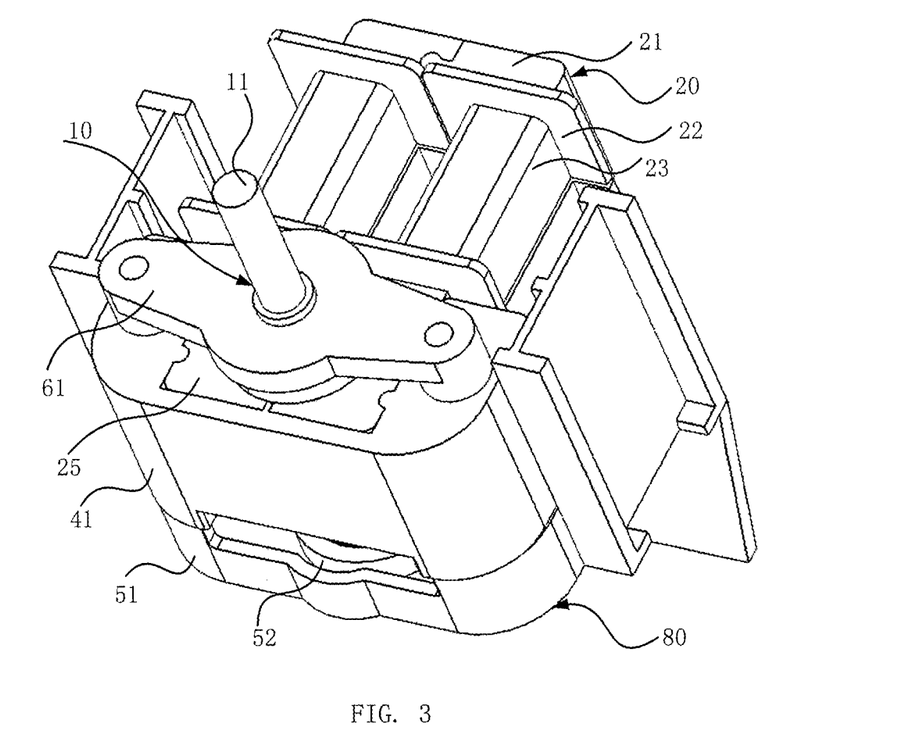
FIG. 3 illustrates a motor of the medical pump of FIG. 1.
Figure 4:
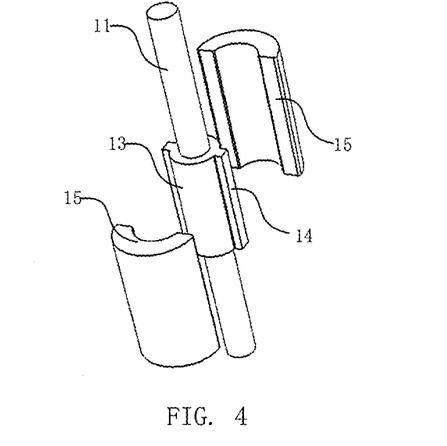
FIG. 4 illustrates a rotor of the motor of FIG. 3.
Figure 7:
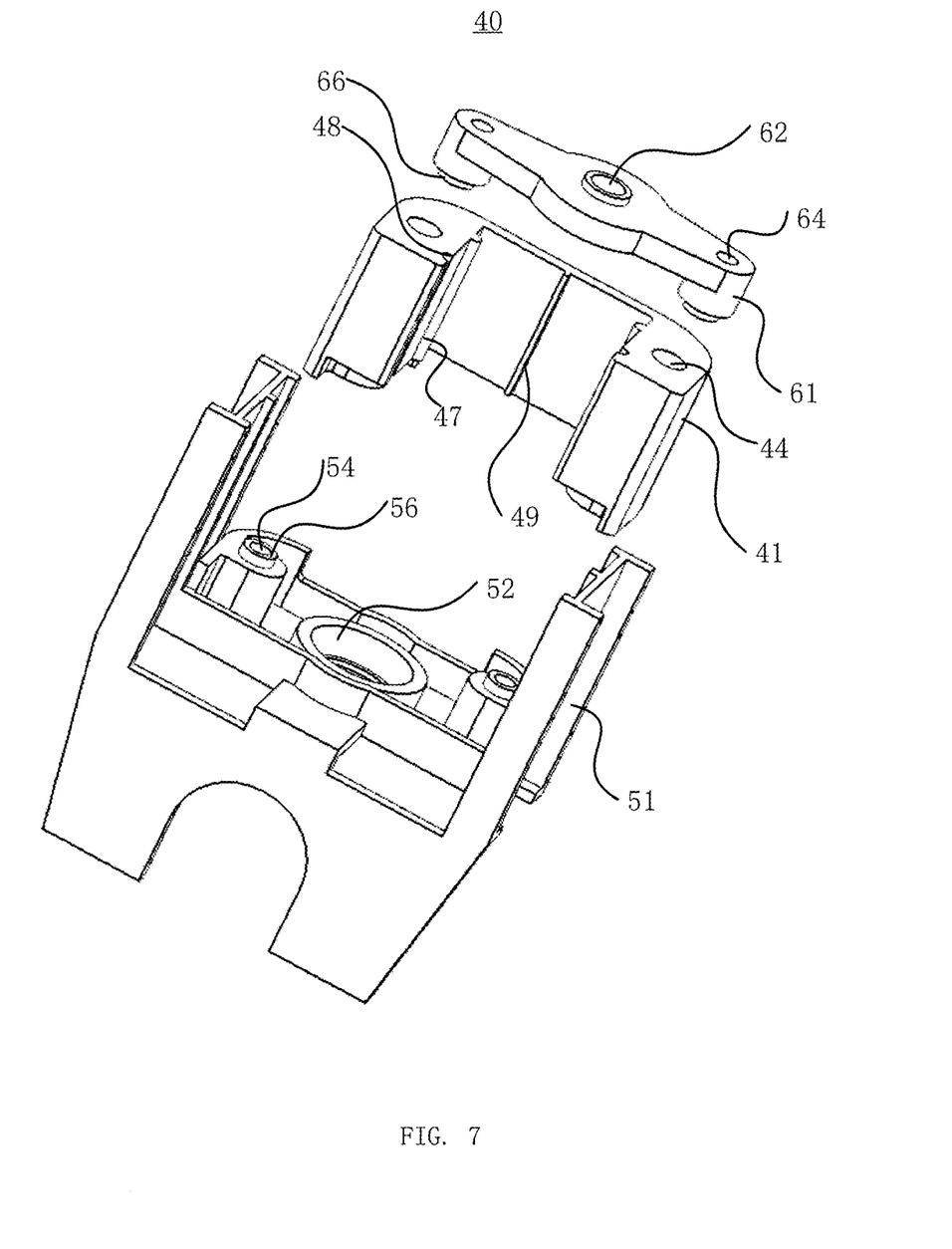
FIG. 7 is an exploded view of the stator fixing member of the motor of FIG. 3.

Referring to FIG. 3 and FIG. 4, the motor 80 is a single phase synchronous motor including a stator 20 and a rotor 10 rotatable relative to the stator 20. The stator 20 includes a stator core 21 and a stator winding 23 wound around the stator core 21. An insulating member is arranged between the stator winding 23 and the stator core 21 for insulating the stator winding 23 and the stator core 21. Specifically, the stator winding 23 is wound around an insulating bracket 22 which is attached around the stator core 21. The stator core 21 is fixed to a stator fixing member 40 (FIG. 7). The rotor 10 is rotatably mounted to the stator fixing member 40. In this embodiment, a rotary shaft 11 of the rotor 10 acts as the output shaft of the motor 80.

The rotor 10 includes a rotor core 13 fixed to the rotary shaft 11 and a plurality of permanent magnets 15 mounted to an outer circumferential surface of the rotor core 13. The permanent magnets 15 are disposed along a circumferential direction of the rotor core 13. The outer circumferential surface of the rotor core 13 is further provided with a plurality of axially-extending ribs 14 each located between corresponding two adjacent permanent magnets 15. In this embodiment, there are two arcuate permanent magnets 15 that are radially polarized, and the number of the ribs 14 is also two. In an alternative embodiment, the permanent magnets may be directly fixed to the rotary shaft. In the alternative embodiment, each permanent magnet 15 forms one permanent magnetic pole. It should be understood that multiple permanent magnets 15 can cooperatively form one permanent magnetic pole.

Figure 5:
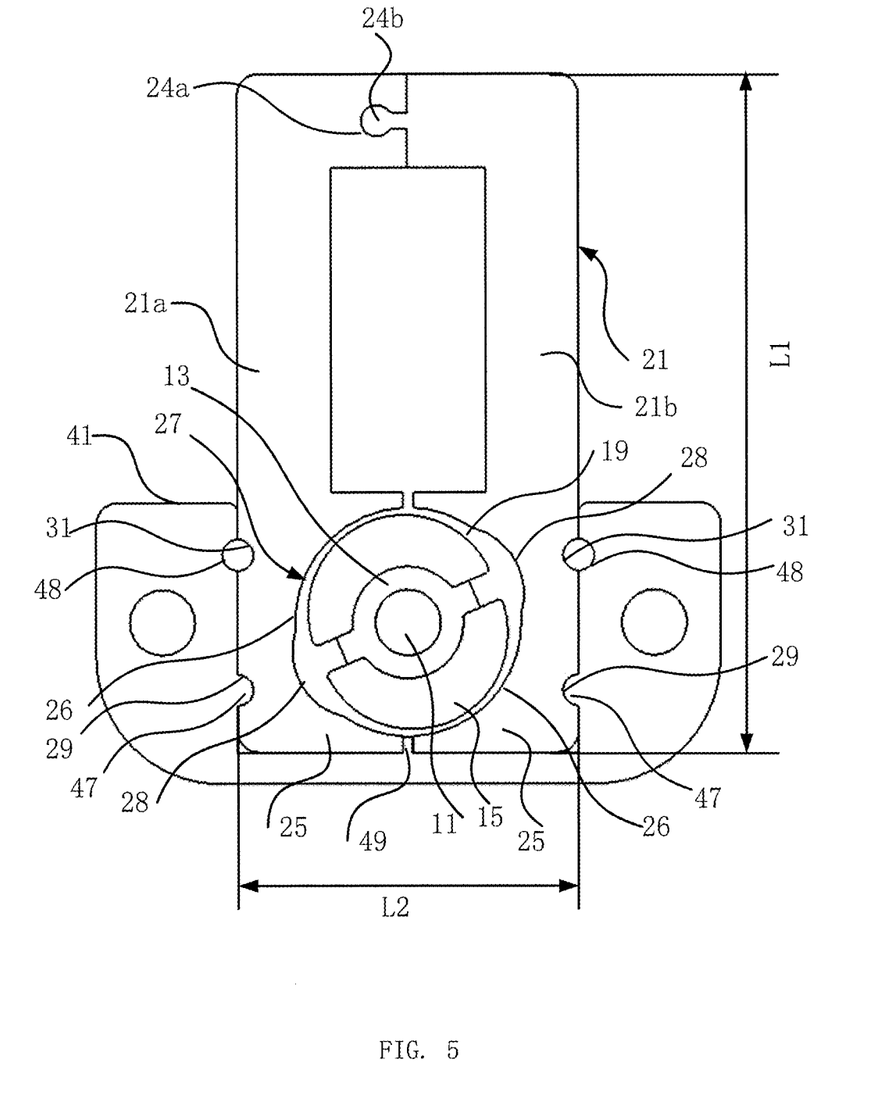
FIG. 5 is a top plane view of the motor of FIG. 3 with a frame and cover of a stator fixing member being removed.
Figure 6:
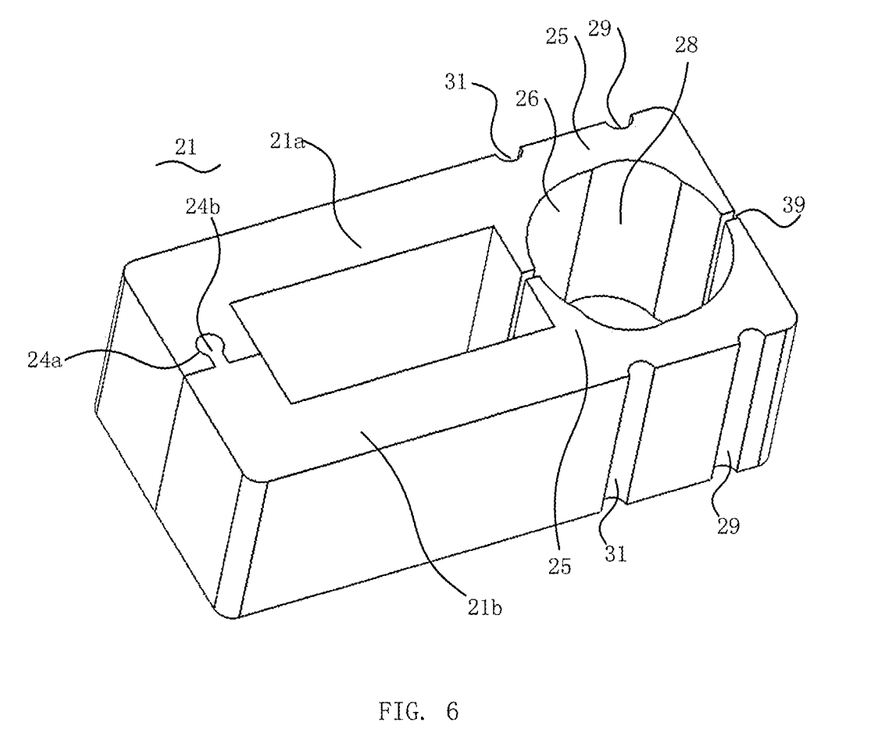
FIG. 6 illustrates a stator core of the motor of FIG. 3.

Referring to FIG. 5 through FIG. 7, the stator core 21 includes two opposing pole portions 25. The two opposing pole portions 25 form therebetween a rotor receiving space 27 for receiving the permanent magnets 15. In this embodiment, the stator core 21 is approximately a rectangle in a cross sectional view, which includes a [-shaped first core part 21a and a]-shaped second core part 21b that are engaged together in a face-to-face fashion. One end of the first core part 21a and one end of the second core part 21b form a locking recess 24a and a dovetailed projection 24b, respectively, and are engaged with each other through interlocking between the locking recess 24a and the dovetailed projection 24b. The other ends of the first core part 21a and the second core part 21b form the corresponding pole portions 25, respectively. Each pole portion 25 has a concaved, arc pole face 26. The two pole faces 26 are opposed to each other and define therebetween the rotor receiving space 27 for receiving the rotor. The pole face 26 forms a positioning groove 28 concaved therefrom. Thus, the distance from the area of the pole face 26 where the positioning groove 28 are located to the rotor axis is larger than the distance from the other area of the pole face 26 to the rotor axis. When the stator winding is not energized, the rotor can be positioned at an initial position where the radial middle of the rotor magnetic pole 15 of the motor is offset from the radial middle of one corresponding stator pole portion 25 due to existing of the positioning grooves 28. The stop position or initial position of the rotor can be controlled such that the stop position of the rotor is offset from a dead point position (where the radial middle of the rotor pole is aligned with the radial middle of the stator pole portion). The positioning groove 28 extends continuously or discontinuously along an axial direction of the motor. Preferably, the positioning groove 28 is offset from the center of the stator pole portion 25, making the rotor startup easier in one direction than the other opposing direction. Preferably, most portions of the pole face 26 are located on a same cylindrical surface that is concentric with the rotor, except for the area of the positioning groove. Preferably, the stator core 21 has a length L1 in the range of 60 mm to 70 mm, for example, is 65 mm, and a width L2 in the range of 20 mm to 30 mm.

In this embodiment, an outer surface of each permanent magnet 15 of the rotor 20 is an arc surface, such that an uneven air gap 19 (FIG. 5) is formed between the permanent magnet 15 and the pole portion 25. In a specific embodiment, the permanent magnet 15 may have a thickness decreasing progressively from a circumferential center toward two circumferential ends to cause the distance from the outer circumferential surface of the permanent magnet to the axis of the rotor decreasing progressively from the circumferential center toward two circumferential ends. Thus, the thickness of the air gap 19 between the outer circumferential surface of the permanent magnet of the rotor and the stator pole portion 25 decreases progressively from the circumferential center to two circumferential ends of the permanent magnet 15. Preferably, the outer circumferential surface of the permanent magnet is symmetrical about the circumferential center of the permanent magnet resulting in a substantially symmetrical uneven air gap that is substantially symmetrical about the circumferential center of the permanent magnet 15 except the area where the positioning groove 28 or gap 39 formed between the stator pole portions 25 locates.

The stator core 21 is fixed to a stator fixing member 40 as shown in FIG. 7. The stator fixing member 40 includes a U-shaped bracket 41, a frame 51 fixed to a bottom of the bracket 41, and a cover 61 fixed to a top of the bracket 41. The frame 51 includes a first hub 52. A bearing (not shown) is mounted in the first hub 52, and the rotary shaft 21 is supported by the bearing. The cover 61 includes a second hub 62 that also supports the rotary shaft 21, such that the rotary shaft 21 is rotatable relative to the stator 30. In this embodiment, the bracket 41 has first through holes 44 extending in the axial direction of the motor. The frame 51 and the cover 61 form second through holes 54 and third through holes 64 corresponding to the first through holes 44. The frame 51 and the cover 61 can be fixed to opposite ends of the bracket 41 by connecting members (not shown) that sequentially pass through the through holes 44, 54 and 64. An end of the stator core 21 that has the pole portions 25 is fixed to and surrounded by the U-shaped bracket 41, and is axially positioned between the frame 51 and the cover 61.

In order to facilitate the positioning and assembly between the bracket 41, the frame 51 and the cover 61, the frame 51 form a first protruding ring 56 at an end of the second through hole 54. The first protruding rings 56 can be inserted into the first through holes 44 of the bracket 41. Preferably, the first protruding rings 56 have a slightly tight-fit with inner wall surfaces of the first through holes 44. Similarly, the cover 61 form second protruding rings 66 at ends of the third through holes 64. The second protruding rings 66 can be inserted into the first through holes 44 of the bracket 41. Preferably, the second protruding rings 66 have a slightly tight-fit with the inner wall surfaces of the first through holes 44. In assembly, the bracket 41 is mounted to the frame 51, with the first protruding rings 56 inserted into lower end portions of the first through holes 44. The stator core 21 and rotor are then mounted to the bracket 41 and the shaft 11 of the rotor is inserted into the hub 52 of the frame 51. The cover 61 is then mounted, with the second protruding rings 59 inserted into upper end portions of the first through holes 44, thereby fixedly assembling the bracket 41, the frame 51, the stator 20, the rotor 10 and the cover 61 together.

The U-shaped bracket 41 is attached around an outer periphery of one end of the stator core 21 that forms the rotor receiving space 27. Preferably, a concave-convex locking structure is formed between the stator core 21 and the bracket 41 to lock the connection therebetween. Referring also to FIG. 5, in this embodiment, a plurality of axial first grooves 29 and second grooves 31 are formed in the outer periphery of the stator core 21, an inner wall surface of the bracket 41 forms a plurality of first ribs 47 for engaging with the first grooves 29 to form the concave-convex locking structure. Inner surfaces of the first grooves 29 are smooth arc surfaces, and outer surfaces of the first ribs 47 are also smooth arc surfaces. The first ribs 47 and the first grooves 29 cooperatively form a guiding structure which facilitates mounting the stator core 21 to the bracket 41. The inner wall surface of the bracket 41 further forms a plurality of third grooves 48 for cooperating with the second grooves 31 to form through holes, and these through holes can be used to position and fix the stator core and ensure concentricity between the stator and the rotor.

Preferably, the two opposed pole portions 25 of the stator core are separated apart, in which case, a side wall surface of the U-shaped bracket 41 may be formed with a rib 49 which extends into a gap 39 formed between the two pole portions 25 of the stator core 21. It should be understood that the two opposed pole portions 25 may also be connected together by a magnetic bridge with great magnetic reluctance. The magnetic bridge may be integrally formed with the pole portions 25.

Figure 8:
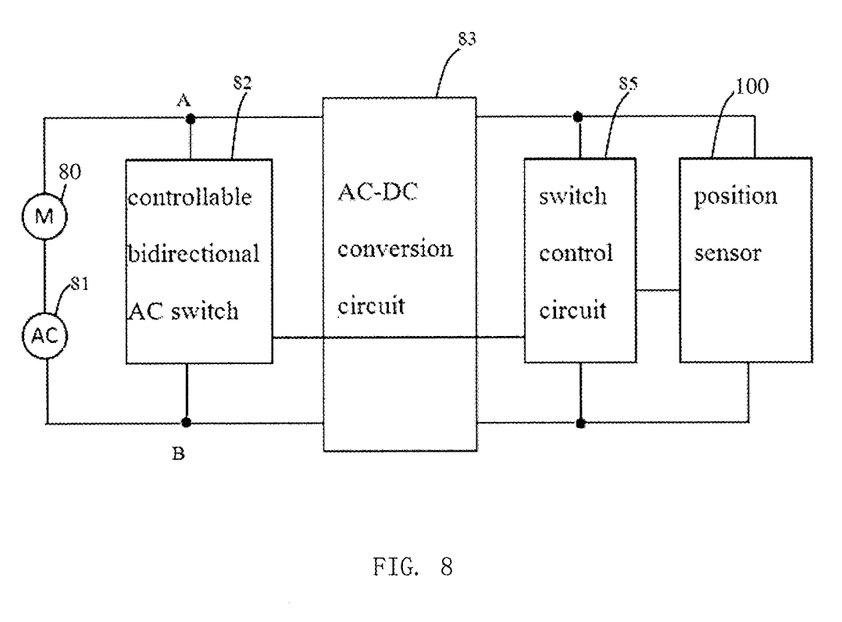
FIG. 8 illustrates a portion of a driving circuit according to one embodiment of the present invention.

FIG. 8 is a block diagram showing a driving circuit of the single phase permanent magnet brushless motor of the present invention. In the driving circuit, the stator windings 23 and an alternating current (AC) power 81 are connected in series between two nodes A and B. The AC power 81 is preferably a commercial AC power supply with a fixed frequency such as 50 Hz or 60 Hz and a supply voltage may be, for example, 110V, 220V or 230V. A controllable bidirectional AC switch 82 is connected between the nodes 84 and 85, in parallel with the series-connected stator windings 23 and AC power 81. The bidirectional AC switch 82 is preferably a triode AC switch (TRIAC) having two anodes connected to the two nodes A and B, respectively. It should be understood that the controllable bidirectional AC switch 82 may be two silicon control rectifiers reversely connected in parallel, and control circuits may be correspondingly configured to control the two silicon control rectifiers in a preset way. An AC-DC conversion circuit 83 is connected between the two nodes A and B, in parallel with the switch 81. An AC voltage between the two nodes A and B is converted by the AC-DC conversion circuit 83 into a low voltage DC. A position sensor 20 is used to sense the position of the rotor and the position sensor 20 may be powered by the low voltage DC power outputted from the AC-DC conversion circuit 83, for detecting the position of the magnetic poles of the permanent magnet rotor 14 of the synchronous motor 10 and outputting corresponding signals. A switch control circuit 85 is connected with the AC-DC conversion circuit 83, the position sensor 20 and the bidirectional AC switch 82, and is configured to control the bidirectional switch 82 to switch between a switch-on state and a switch-off state in a predetermined way, based on the magnetic pole position of the permanent magnet rotor and the polarity of the AC power source, such that the stator winding 23 urges the rotor to rotate only in the above-mentioned fixed starting direction during a starting phase of the motor. In this embodiment, in a case that the controllable bidirectional AC switch 82 is switched on, the two nodes A and B are short-circuited, and the AC-DC conversion circuit 83 does not consume electric energy because there is no electrical current flows through the AC-DC conversion circuit 83, hence, the utilization efficiency of electric energy can be improved significantly.

When the stator winding and the external AC power are connected in series, the single phase synchronous motor 50 of the present invention has an input power of 45 W to 50 W, and an electrical current of 0.4 A to 0.6 A. The rotor 20 of the motor can rotate at a constant speed of 2800 RPM to 3800 RPM, such as 3000 RPM, during a steady state. Alternatively, the rotor 20 rotates at a constant speed of 3600 RPM (60 Hz) when the motor is used in another district.

Figure 9:
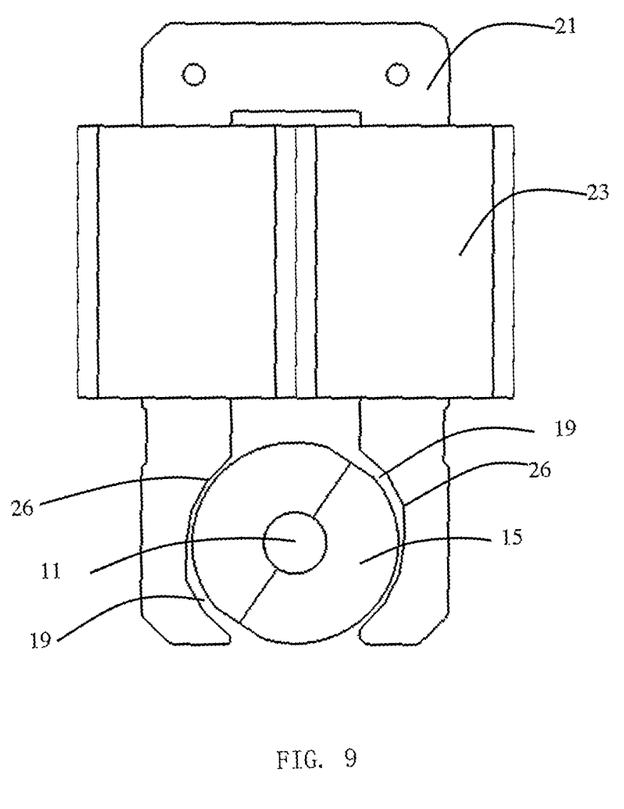
FIG. 9 is a top plane view of a motor according to another embodiment of the present invention.

FIG. 9 is a top plane view of a motor according to another embodiment of the present invention.

In this embodiment, the radial outer surface of each permanent magnet 15 includes an arc surface portion and plane surface portions at two ends of the arc surface portions. The plane surface portions of the two permanent magnets are connected and coplanar. The arc surface portions of the two permanent magnets are preferably located on a same cylindrical surface that is concentric with the rotary shaft 11. A distance from the pole face 26 of the stator pole portion 25 to a center of the rotary shaft 11 increases progressively from one end to the other end of the pole face 26 along a circumferential direction of the rotor, thereby resulting in an uneven air gap 19 between the rotor permanent magnetic pole 15 and the stator pole portion 25. Preferably, ends of the pole faces 26 of the two stator pole portions 25 that are farthest from the center of the rotary shaft 11 are symmetrical about the center of the rotary shaft 11 along the radial direction. Preferably, the rotor permanent magnetic pole 15 has a pole-arc coefficient of 0.75 to 0.95 and, more preferably, 0.9 to 0.95. In this embodiment, the used of two separate arcuate permanent magnetic poles 15 makes the permanent magnetic pole 15 have a greater pole-arc angle, which reduces the cogging torque of the motor to make the rotation of the rotor smoother and reduces cost in comparison with the integral ring magnet.

It should be understood that the rotor of this embodiment may also use the permanent magnetic pole as used in the above embodiment, i.e. the thickness of the permanent magnetic pole 15 decreases progressively from the circumferential center toward the two circumferential ends, such that the thickness of the air gap 19 increases progressively from the circumferential center toward the two circumferential ends of the permanent magnetic pole 15.

The medical pump of the present invention has a simplified structure and reduced size, which effectively reduces cost. In addition, the motor of the medical pump has a constant rotation speed which is immune to voltage variations. The medical pump is particularly suitable for use in atomizers, which has a constant motor speed and outputs stable air pressure to deliver more uniform spray. In addition, the motor has a high efficiency and has a smaller size and less weight under the same output power conditions as traditional motors used in medical pump.

Although the invention is described with reference to one or more embodiments, the above description of the embodiments is used only to enable people skilled in the art to practice or use the invention. It should be appreciated by those skilled in the art that various modifications are possible without departing from the spirit or scope of the present invention. The embodiments illustrated herein should not be interpreted as limits to the present invention, and the scope of the invention is to be determined by reference to the claims that follow.

The invention claimed is:
1. A medical pump comprising:
a single phase synchronous motor comprising a stator and a rotor rotatable relative to the stator, the rotor comprising a plurality of permanent magnets, the stator comprising a stator core and a winding wound around the stator core,
wherein the medial pump further comprises an AC-DC conversion circuit and a bidirectional AC switch, an external AC power and the stator winding of the motor are connected in series between a first node and a second node, and the AC-DC conversion circuit and the bidirectional AC switch are connected in parallel between the first node and the second node.
2. The medical pump of claim 1, wherein the stator core comprises two opposed pole portions that define therebetween a receiving space, and the permanent magnets are received in the receiving space and forms two permanent magnetic poles facing the pole portions of the stator.
3. The medical pump of claim 2, wherein an outer surface of each of the permanent magnets is an arc surface and the permanent magnets of the rotor and the pole portions of the stator define therebetween an air gap with an uneven thickness.
4. The medial pump of claim 3, wherein the air gap is substantially symmetrical about a circumferential center of the permanent magnet poles.
5. The medial pump of claim 2, wherein a distance from an outer surface of each of the permanent magnetic poles to an axis of the rotor decreases progressively from a circumferential center toward two circumferential ends of the outer surface of the permanent magnetic pole, and a thickness of the air gap increases progressively from the circumferential center toward the two circumferential ends of the permanent magnetic pole.
6. The medial pump of claim 2, wherein the medical pump further comprises a U-shaped bracket, the bracket surrounds an end of the stator core that defines the two pole portions.
7. The medial pump of claim 6, wherein outer surfaces of the stator core form first grooves or ribs, inner surfaces of the bracket form first ribs or grooves, and the first grooves and the first ribs are engaged to attach the stator core to the bracket.

8. The medial pump of claim 6, wherein the two opposed pole portions are separated apart, the bracket forms a rib that extends into a gap formed between the two opposed pole portions.
9. The medial pump of claim 6, wherein the stator further comprises a frame and a cover respectively mounted to a bottom and a top of the bracket, the stator core is axially positioned between the frame and the cover, and the rotor is rotatably mounted to the frame and the cover.
10. The medial pump of claim 2, wherein the stator core comprises a [-shaped first core part and a]-shaped second core part that are spliced in a face-to-face fashion, a first end of the first core part and a first end of the second core part respectively form the pole portions, a second end of the first core part and a second end of the second core part are connected with each other.
11. The medial pump of any of claim 2, wherein a distance of a pole face of each stator pole portion to a center of a rotary shaft increases progressively from one end to the other end of the pole face along a circumferential direction of the rotor.
12. The medial pump of claim 1, wherein the rotor rotates at a constant speed of 3000 RPM or 3600 RPM during a steady state.
13. The medial pump of claim 1, wherein the synchronous motor has an input power of 45 W to 50 W and an electrical current of 0.4 A to 0.6 A, and the stator core has a length L1 of 50 mm to 65 mm and width L2 of 20 mm to 30 mm.
14. The medial pump of claim 1, wherein the permanent magnets form two permanent magnetic poles having a pole-arc coefficient of 0.75 to 0.95.
15. The medial pump of any of claim 1, wherein the pump further comprises a rod piston driven by the single phase synchronous motor and a cylinder for receiving the rod piston for reciprocating motion therein.
16. A medical pump comprising: a single phase synchronous motor comprising a stator and a rotor rotatable relative to the stator, the rotor comprising a plurality of permanent magnets, the stator comprising a stator core and a winding wound around the stator core,
wherein the single phase motor further comprises a driving circuit, the stator winding is adapted to be connected in series with an AC power source between a first node and a second node, the driving circuit comprises:
a controllable bidirectional AC switch connected between the first node and the second node;
an AC-DC conversion circuit connected in parallel with the controllable bidirectional AC switch between the first node and the second node;
a position sensor configured to detect a magnetic pole position of the permanent magnet rotor; and
a switch control circuit configured to control the controllable bidirectional AC switch to be switched between a switch-on state and a switch-off state in a predetermined way, based on the magnetic pole position of the permanent magnet rotor and a polarity of the AC power source such that the stator winding drives the rotor to rotate only in the predetermined direction,
wherein there is no current flowing through the AC-DC conversion circuit when the first node and the second node are short circuited by the controllable bidirectional AC switch.
17. A medical pump comprising:
a single phase synchronous motor comprising a stator and a rotor rotatable relative to the stator, the rotor comprising a plurality of permanent magnets, the stator comprising a stator core and a winding wound around the stator core, wherein the stator core comprises two opposed pole portions that define therebetween a receiving space, and the permanent magnets are received in the receiving space and forms two permanent magnetic poles facing the pole portions of the stator, wherein a distance from an outer surface of each of the permanent magnetic poles to an axis of the rotor decreases progressively from a circumferential center toward two circumferential ends of the outer surface of the permanent magnetic pole, and a thickness of the air gap increases progressively from the circumferential center toward the two circumferential ends of the permanent magnetic pole.

* * * * *